US006428968B1

(12) United States Patent
Molnar-Kimber et al.

(10) Patent No.: US 6,428,968 B1
(45) Date of Patent: Aug. 6, 2002

(54) COMBINED THERAPY WITH A CHEMOTHERAPEUTIC AGENT AND AN ONCOLYTIC VIRUS FOR KILLING TUMOR CELLS IN A SUBJECT

(75) Inventors: Katherine Molnar-Kimber, Worcester; Larry Kaiser, Wynnewood; Takane Toyoizumi, Philadelphia, all of PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 0 days.

(21) Appl. No.: 09/435,797

(22) Filed: Nov. 8, 1999

Related U.S. Application Data

(63) Continuation of application No. PCT/US99/05536, filed on Mar. 13, 1999.

(51) Int. Cl.[7] .......................... G01N 33/574; C12Q 1/70
(52) U.S. Cl. ........................................... 435/7.23; 435/5
(58) Field of Search ..................... 435/5, 7.23

(56) References Cited

U.S. PATENT DOCUMENTS

| 4,160,452 A | 7/1979 | Theeuwes ................. 128/260 |
| 4,256,108 A | 3/1981 | Theeuwes ................. 128/260 |
| 4,265,874 A | 5/1981 | Bonsen et al. ............. 424/15 |
| 4,663,308 A | 5/1987 | Saffran et al. ............. 514/3 |
| 4,777,049 A | 10/1988 | Magruder et al. .......... 424/457 |
| 5,585,096 A | 12/1996 | Martuza et al. ............ 424/93.2 |
| 5,728,379 A | 3/1998 | Martuza et al. ............ 424/93.2 |
| 5,772,993 A | 6/1998 | Chung et al. .............. 424/93.6 |

FOREIGN PATENT DOCUMENTS

| CA | 50523/74 | 7/1990 |
| JP | 7233079 A | 2/1994 |

OTHER PUBLICATIONS

Brown et al., 1994, J. Gen. Virol. 75:3767–3686.
Chambers et al., 1995, Proc. Natl. Acad. Sci. USA 92:1411–1415.
Chou et al., 1990, Science 250:1262–1265.
Coukos et al., 1998, Gene Ther. Mol. Biol. 3:79–89.
Elias, 1993, Chest 103(4 Supp.):362S–366S.
Fauci et al., 1998, In: *Principals of Internal Medicine*, 14th ed., McGraw–Hill Co., Inc., pp. 552–562.
Friend et al., 1984, J. Med. Chem. 27:261–268.
Galvan et al., 1998, Proc. Natl. Acad. Sci. USA 95:3931–3936.
Green, 1993, Chest 103(4 Supp.):370S–372S.
Heise et al., 1997, "Preclinical studies with ONYX–015 {a replication competent E1B–deleted adenovirus} in combination with chemotherapy," Abstract, The Sixth International Conference on Cancer Gene Therapy, Nov. 20–22, 1997, San Diego CA.

(List continued on next page.)

Primary Examiner—Hankyel T. Park
(74) Attorney, Agent, or Firm—Morgan, Lewis & Bockius, LLP

(57) ABSTRACT

The invention includes methods, compositions, and kits for killing tumor cells in a subject such as a human patient. The methods comprise administering both a chemotherapeutic agent and an oncolytic virus other than an adenovirus to a subject which has tumor cells. The agent and virus exhibit oncolytic activities that are at least additive, and that may be synergetic. The oncolytic virus may, for example, be a herpes simplex virus (type 1 or 2), a vaccinia virus, a vesicular stomatitis virus, or a Newcastle disease virus. The compositions and kits comprise a chemotherapeutic agent and an oncolytic virus other than an adenovirus, either in admixture or separately.

19 Claims, 2 Drawing Sheets

OTHER PUBLICATIONS

Jett, 1993, Mayo Clin. Proc. 68:603–611.
Johnson, 1994, Chest 106(6 Supp.):313S–317S.
Kirn et al., 1999, In: *Gene Therapy of Cancer*, Academic Press, San Diego, CA, pp. 235–248.
Kucharczuk et al., 1997, Cancer Res. 57:466–471.
MacLean et al., 1991, J. Gen. Virol. 72:630–639.
Market et al., 1992, J. Neurosurg. 77:590–594.
Martuza et al., 1991, Science 252:854–856.
Meignier et al., 1988, J. Infect. Dis. 158:602–614.
Midthun et al., 1997, Postgrad. Med. 101:187–194.
Mineta et al., 1995, Nature Med. 1:938–943.
Montgomery et al., 1996, Cell 87:427–436.
Nesbitt et al., 1995, Ann. Thorac. Surg. 60:466–72.
Nielsen et al., 1997, "Adenovirus–mediated p53 gene therapy synergizes with paclitaxel against human ovarian, mammary, prostate, head and neck, and liver cancer," Abstract, The Sixth International Conference on Cancer Gene Therapy, Nov. 20–22, 1997, San Diego CA.
Parker et al., 1997, CA Cancer J. Clin. 47:5–27.
Randazzo et al., 1995, Virology 211:94–101.
Robertson et al., 1992, J. Gen. Virol. 73:967–970.
Rodriguez et al., 1997, Cancer Res. 57:2559–2563.
Shaw et al., 1993, Mayo Clin. Proc. 68:593–602.

COMBINED THERAPY WITH A CHEMOTHERAPEUTIC AGENT AND AN ONCOLYTIC VIRUS FOR KILLING TUMOR CELLS IN A SUBJECT

CROSS-REFERENCE TO RELATED APPLICATIONS

This application is a continuation of International Application PCT/US99/05536, which was filed on Mar. 13, 1999.

STATEMENT REGARDING FEDERALLY SUPPORTED RESEARCH OR DEVELOPMENT

This research was supported in part by U.S. Government funds (NIH grant number CA 66726-S1), and the U.S. Government may therefore have certain rights in the invention.

FIELD OF THE INVENTION

The field of the invention is killing tumor cells in a subject.

BACKGROUND OF THE INVENTION

Cancer remains one of the leading causes of morbidity and mortality of humans worldwide. Known cancer therapies include chemotherapy, radiation, surgery, and gene therapy. The combined use of chemotherapy, radiation, and surgery has augmented the benefits of these therapies in some types of cancer, but in only a few types of cancer has it resulted in eradication of the tumor. Despite the promise afforded by gene therapy anti-cancer strategies, various shortcomings in virus vectors and other gene vectors have limited the efficacy of gene therapy methods for eradicating tumor cells from subjects such as humans afflicted with cancer.

Recent advances in virology and molecular biology have made possible the engineering of recombinant virus with specific properties, creating new interest in virus-based therapy of solid tumors. One promising approach is the use of genetically modified herpes simplex virus-1 (HSV-1) to treat central nervous system (CNS) malignancies (Mineta et al., 1995, Nature Med. 1:938–943; Martuzza et al., 1991, Science 252:854–856; Market et al., 1992, J. Neurosurg. 77:590–594; Randazzo et al., 1995, Virology 211:94–101; Kesari et al., 1995, Lab. Invest. 73:636–648). Mutant HSV-1 viruses, such as HSV-1716, HSV-3616, HSV-4009, HSV-3410 and HSV-G207 have a deletion or impaired function in the gene encoding ICP34.5 which is a major determinant of pathogenicity (MacLean et al., 1991, J. Gen. Virol. 72:630–639; Chambers et al., 1995, Proc. Natl. Acad. Sci. USA 92:1411–1415; Meignier et al., 1988, J. Infect. Dis. 158:602–614; Mineta et al., 1995, Nature Med. 1:938–943).

Mutation of ICP34.5 affects host protein shut-off. These mutants have markedly attenuated neurovirulence and can replicate much more efficiently in dividing cells and malignant cells than in non-dividing cells (MacLean et al., 1991, J. Gen. Virol. 72:630–639; Robertson et al., 1992, J. Gen. Virol. 73:967–970; Brown et al., 1994, J. Gen. Virol. 75:3767–3686; Chou et al., 1990, Science 250:1262–1265).

Although most studies of oncolytic HSV-1 viruses have involved treatment of CNS malignancies, it has been shown that such viruses are also effective for treatment of localized non-CNS malignancies (e.g. malignant mesothelioma and non-small cell lung cancer) in vitro and in vivo. Lung tissue, for example, is a tissue which expresses high level of HSV receptors (Montgomery et al., 1996, Cell 87:427–436). The ability to use HSV-1 mutant virus to treat patients with non-small cell lung cancer has significant clinical importance. However, prior art methods of using oncolytic viruses are limited by, among other things, the efficacy of the viruses for killing tumor cells.

HIV-1716 is a replication-competent herpes simplex virus type 1 which has a 759-bp deletion in both copies of the RL1 portion of its genome at a gene which encodes the protein ICP34.5. Viruses with this mutation exhibit drastically reduced neurovirulence. These viruses do not cause encephalitis when inoculated either intracerebrally or peripherally into a host. Moreover, these mutants replicate as well as their wild-type parental strain (e.g. 17+) in a variety of dividing cells lines, but replicate poorly in cells not undergoing mitosis. These characteristics make HSV-1716 and other RL1 mutants attractive as vectors for cancer gene therapy.

Previous studies have demonstrated that RL1 mutant herpesviruses like HSV-1716 replicate well in established dividing human glioma cell lines, as well as in primary cell cultures derived from human biopsy material. Infection of these cultures result in cell death in the majority of cases. It is also believed that, in some cell lines, premature shut-off of host protein synthesis occurs in response to a lack of expression of ICP34.5. This has been designated "the double hit phenomenon." In vivo studies involving these viruses have also been encouraging. Several groups have demonstrated oncolytic efficacy in both immunocompromised and immunocompetent mouse models of intracranial malignancies. Furthermore, it has been shown that HSV antigen staining is restricted to the tumor weight, with no spread to adjacent normal tissue.

Similar studies have been performed in animal models of malignant mesothelioma, a uniformly fatal neoplasia of the lining of the pleural cavity which does not respond well to surgery, chemotherapy or radiation. Kucharczuk et al. (1997, Cancer Res. 57:466–471) demonstrated that several nonneuronally derived human cell lines support HSV-1716 growth in vitro. Furthermore, their in vivo study was based on a well-characterized intraperitoneal model of human malignant mesothelioma involving REN cells injected into SCID mice. Those results demonstrated reduced tumor burden and significantly prolonged survival after intraperitoneal injection of HSV-1716 into tumor-bearing animals. Still, however, tumor cells were not completely eradicated from the test subjects. Thus, the subjects were not cured of cancer, even though their tumor burden was significantly reduced. It follows that although such therapies are useful for treating cancer, these therapies remain amenable to improvement, and that supplemental treatments may remain necessary to prevent re-establishment of nearly ablated tumors, to kill residual tumor cells following surgical tumor excision, and to inhibit growth of immature metastases by killing tumor cells distributed throughout the body of a subject.

Although malignant mesothelioma lends itself to study because of its location in the lining of the pleural cavity, there is interest in other, more prevalent, thoracic malignancies which have poor prognoses unless identified early. Other malignancies in which morbidity is associated with localized disease include, for example, bronchoalveolar cell, bladder, endometrial, cervical, and ovarian cancers.

Currently, lung cancer is the leading cause of cancer death in the United States, with an estimated incidence and mortality of 178,100 cases and 160,400 deaths, respectively (data from 1997; Parker et al., 1997, CA Cancer J. Clin.

47:5–27). The prognoses for lung cancer patients are still very poor, and most patients die within one year of diagnosis. At the time of diagnosis, only 15% of all lung cancer patients have local disease, 25% have disease spread to the regional lymph nodes, and 55% have distant metastatic cancer. Even in patients having localized disease, the 5-year survival rate is only 48%, survival is 18% for patients having regional disease and 14% overall (Fauci et al., 1998, In: *Principals of Internal Medicine,* 14th ed., McGraw-Hill Co., Inc., pp. 552–562). Although chemotherapy, radiotherapy, or both, are often given to patients having inoperable disease, traditional therapy does not offer much clinical value to the majority of patients (Midthun et al., 1997, Postgrad. Med. 101:187–194; Nesbitt et al., 1995, Ann. Thorac. Surg. 60:466–72; Johnson, 1994, Chest 106(6 Supp.):313S–317S; Green, 1993, Chest 103(4 Supp.):370S–372S; Jett, 1993, Mayo Clin. Proc. 68:603–611; Elias, 1993, Chest 103(4 Supp.):362S–366S; Shaw et al., 1993, Mayo Clin. Proc. 68:593–602).

Taken together, these studies demonstrate that use of various oncolytic viruses to kill tumor cells is well accepted, even if prior art uses of such oncolytic vectors have been plagued with shortcomings such as low efficacy, low tissue specificity, rapid clearing of oncolytic viruses, and inability to deliver a sufficiently high or prolonged doses of virus to the desired tumor tissue. The present invention overcomes the shortcomings of prior art anti-cancer therapies involving oncolytic viruses by improving the efficacy of oncolytic virus therapy.

BRIEF SUMMARY OF THE INVENTION

The invention relates to a method of killing tumor cells in a subject having tumor cells. The method comprises administering a chemotherapeutic agent and an oncolytic virus to the subject. Tumor cells in the subject are thereby killed. The oncolytic virus is not an adenovirus.

In one aspect of this method, the chemotherapeutic agent is selected from the group consisting of an anthracycline, an alkylating agent, an alkyl sulfonate, an aziridine, an ethylenimine, a methylmelamine, a nitrogen mustard, a nitrosourea, an antibiotic, an antimetabolite, a folic acid analog, a purine analog, a pyrimidine analog, an enzyme, a podophyllotoxin, a platinum-containing agent, an interferon, and an interleukin. The alkylating agent may, for example, be a bi-functional alkylating agent such as mitomycin C. The folic acid analog may, for example, be a dihydrofolate reductase inhibitor.

Exemplary chemotherapeutic agent useful in the method of the invention include busulfan, improsulfan, piposulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluororacil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elfornithine, elliptinium acetate, etoglucid, etoposide, flutamide, gallium nitrate, hydroxyurea, interferon-alpha, interferon-beta, interferon-gamma, interleukin-2, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofiran, spirogermanium, paclitaxel, tamoxifen, teniposide, tenuazonic acid, triaziquone, 2,2',2"-trichlorotriethylamine, urethan, vinblastine, vincristine, and vindesine.

In another aspect of the invention, the oncolytic virus is selected from the group consisting of a herpes simplex virus-1, a herpes simplex virus-2, a vesicular stomatitis virus, and a vaccinia virus. When the oncolytic virus is a herpes simplex virus-1, it is preferably one which does not express functional ICP34.5. Exemplary strains of herpes simplex virus-1 include HSV-1716, HSV-3410, HSV-3616, HSV-R3616, HSV-R47, HSV-G207, HSV-7020, HSV-NVR10, HSV-G92A, HSV-3616-IL-4, and HSV-hrR3. Exemplary strains of herpes simplex virus-2 include strain 2701, strain 2616, and strain 2604. In a preferred embodiment of the method of the invention, the oncolytic virus is HSV-1716 and the chemotherapeutic agent is mitomycin C.

The method of claim may, for example, be used to kill tumor cells in a mammal such as a human. The tumor cells may, for example, be selected from the group consisting of central nervous system tumor cells, mesothelioma cells, lung cancer cells, non-small cell lung cancer cells, undifferentiated lung carcinoma cells, large cell lung carcinoma cells, adenocarcinoma cells, bronchoalveolar cell lung carcinoma cells, liver cancer cells, localized non-central nervous system tumor cells, solid tumor cells, and ovarian cancer cells.

The invention also relates to pharmaceutical composition comprising a chemotherapeutic agent and an oncolytic virus other than an adenovirus.

The invention further relates to a kit for killing tumor cells in a subject having tumor cells. The kit comprises a chemotherapeutic agent and an oncolytic virus other than an adenovirus. The kit may further comprise an instructional material.

The invention still further relates to use of a chemotherapeutic agent and an oncolytic virus other than an adenovirus for manufacture of a medicament for killing tumor cells in a subject having tumor cells.

The invention yet further relates to use of a chemotherapeutic agent and an oncolytic virus other than an adenovirus for manufacture of a kit for killing tumor cells in a subject having tumor cells.

on day 7, and PBS was intravenously administered to these mice on day 8. Cell culture medium was injected into the tumors of the third group of mice ("MMC only") on day 7, and PBS comprising mitomycin C was intravenously administered to these mice on day 8. Cell culture medium comprising HSV-1716 was injected into the tumors of the first group of mice ("MMC+1716") on day 7, and phosphate buffered saline PBS comprising mitomycin C was intravenously administered to these mice on day 8.

Figure 2:
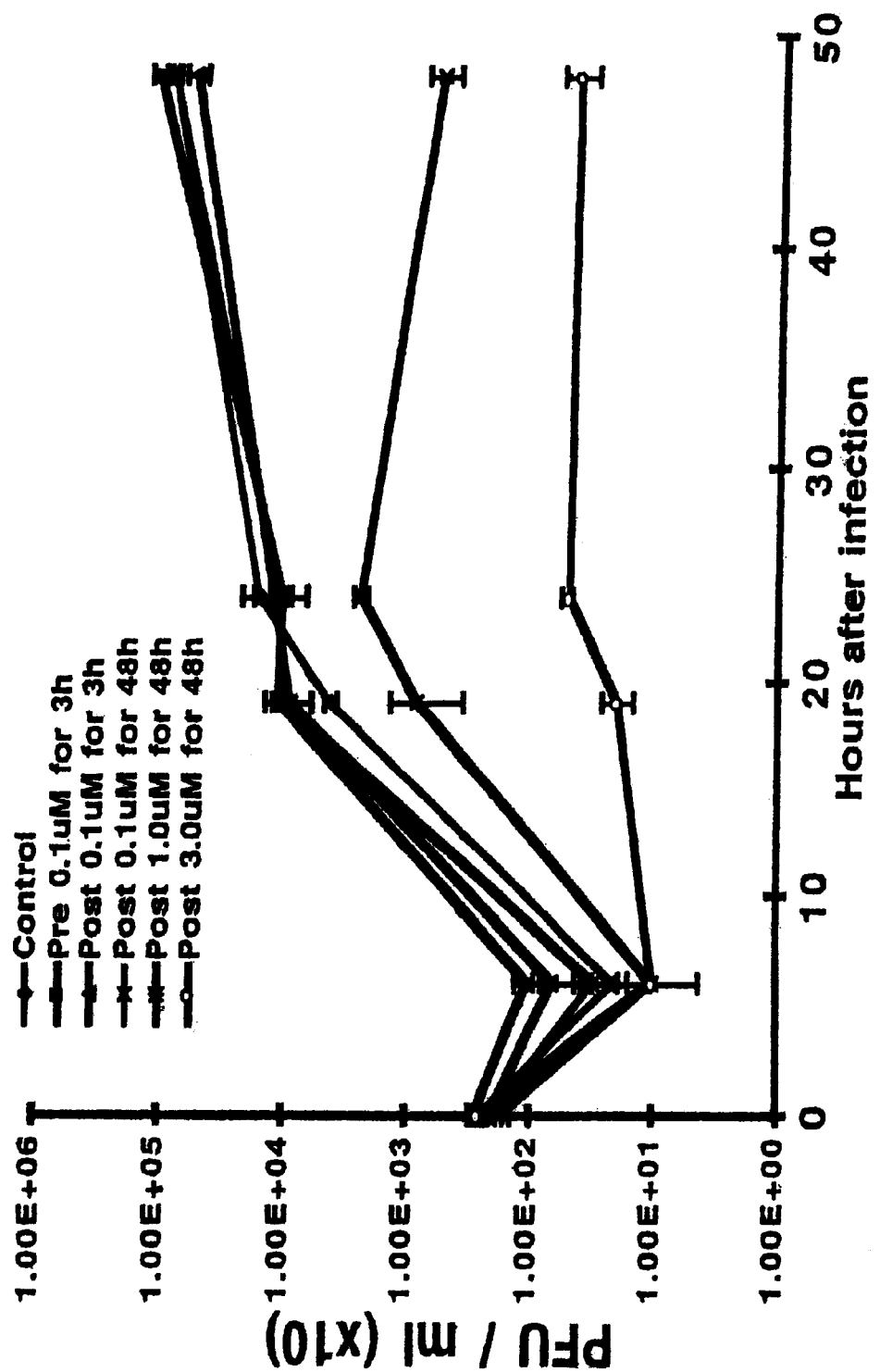

FIG. 2 is a graph which depicts the effect of the timing and concentration of mitomycin C exposure on the burst size of H460 cells infected with HSV-1716.

DETAILED DESCRIPTION

The invention is based on the discovery that administration of both an oncolytic virus and a chemotherapeutic agent to a subject having tumor cells results in a greater extent of tumor cell death in the subject than administration of either the viruses or agent alone. Furthermore, it was, surprisingly, discovered that the effects of administration of both an oncolytic virus and a chemotherapeutic agent are, under certain circumstances, synergistic, and not simply additive. The invention therefore includes methods, compositions, and kits for administering both a chemotherapeutic agent and an oncolytic virus other than an adenovirus to a subject having tumor cells. The oncolytic virus is preferably a mutant or engineered herpes simplex virus. Other related aspects of the invention will be apparent to the skilled artisan in view of the present disclosure.

Definitions

As used herein, each of the following terms has the meaning associated with it in this section.

The articles "a" and "an" are used herein to refer to one or to more than one (i.e. to at least one) of the grammatical object of the article. By way of example, "an element" means one element or more than one element.

A "subject" is an animal, preferably a mammal such as a human.

A subject "has tumor cells" if the subject comprises or is suspected to comprise tumor cells in any form (i.e. in the form of a solid tumor, a dispersed tumor, a metastatic tumor cell, or the like).

A tumor cell is "killed" if it is induced to lyse, if it is induced to undergo apoptosis, or if it is rendered incapable of growing or dividing.

A "chemotherapeutic agent" is any chemical compound which is able to kill a tumor cell without it being necessary for the compound to first be transcribed or reverse-transcribed to generate a transcribed nucleic acid.

An "oncolytic virus" is any virus which is able to kill a tumor cell by infecting the tumor cell.

By describing two polynucleotides as "operably linked" as used herein is meant that a single-stranded or double-stranded nucleic acid moiety comprises each of the two polynucleotides and that the two polynucleotides are arranged within the nucleic acid moiety in such a manner that at least one of the two nucleic acid sequences is able to exert a physiological effect by which it is characterized upon the other.

As used herein, a "functional" biological molecule is a biological molecule in a form in which it exhibits a property by which it is characterized. A functional enzyme, for example, is one which exhibits the characteristic catalytic activity by which the enzyme is characterized.

An oncolytic virus is "replication-selective" if it is more capable of replicating or is capable of replicating to a greater extent (e.g. burst size) in a tumor cell of a subject than in a non-tumor cell of the subject.

Description

Surgery, chemotherapy, and radiotherapy are often combined to augment their therapeutic effect in the clinic. However, no evaluation of combining oncolytic virus administration (other than adenovirus) and administration of chemotherapeutic agents has been performed until the present disclosure. As described herein, administration of a combination of a chemotherapeutic agent (e.g. mitomycin C, methotrexate, cisplatinum, or doxorubicin) and an oncolytic virus (e.g. a mutant herpes simplex virus such as HSV-1716) results in a tumor cell-killing effect that is at least additive and that is, in certain circumstances, synergistic. Although these results are presented herein in the form of data relating to various human lung cancer cell lines, the known susceptibility of other types of cancers to the same chemotherapeutic agents and oncolytic viruses indicates that the combined effect may be expected to be manifested in cancers of all sorts when these agents and viruses are administered in combination to subject having tumor cells of all types.

Previously described combined therapies involving an adenovirus and a chemotherapeutic agent were as follows. Combination therapy with non-replicating adenovirus-mediated p53 gene therapy and chemotherapeutic agents such as paclitaxel or 5-fluorouracil (5-FU) was demonstrated (Gjerset et al., 1997, Cancer Gene Ther.; Nielsen et al., 1997, "Adenovirus-mediated p53 gene therapy synergizes with paclitaxel against human ovarian, mammary, prostate, head and neck, and liver cancer," Abstract, The Sixth International Conference on Cancer Gene Therapy, Nov. 20–22, 1997, San Diego, Calif.). Combination therapy with replication competent E1B-deleted adenovirus-mediated gene therapy and chemotherapeutic agents such as 5-fluorouracil, cisplatinum, and CPT-11 was also demonstrated (Heise et al., 1997, "Preclinical studies with ONYX-015 {replication competent E1B-deleted adenovirus} in combination with chemotherapy," Abstract, The Sixth International Conference on Cancer Gene Therapy, Nov. 20–22, 1997, San Diego, Calif.).

HSV mutants have been used for oncolytic treatment, but combination therapy involving administration of both an HSV mutant and a chemotherapy agent to a subject has not been taught or suggested by others.

Combining traditional chemotherapy with administration of an oncolytic virus has several potential benefits. First, as demonstrated herein, administration of a combination of a chemotherapeutic agent and an oncolytic virus achieves a stronger cytotoxic effect on tumor cells than administration of either the agent or the virus alone. Second, use of combination therapy reduces the necessary dose of both the agent and the virus, thus lessening the morbidity associated with each. Third, use of smaller doses of oncolytic viruses decreases side-effects associated with use of such viruses in subjects. Furthermore, use of smaller doses of oncolytic viruses and chemotherapeutic agents decreases the cost of these expensive forms of anti-cancer therapy. Such combined therapy may be particularly useful for subjects who have inoperative and/or recurrent cancers which have proven resistant to conservative therapies.

The invention includes a method of killing tumor cells in a subject having tumor cells. The method comprises administering to the subject both a chemotherapeutic agent and an oncolytic virus other than an adenovirus. Administration of both the agent and the virus causes tumor cell death in the subject. The order in which the agent and the virus are administered is not critical. The agent may be administered before, after, or at the same time as the virus. What is important is that the agent and virus be administered to the subject sufficiently closely in time that the period during which the oncolytic effects of the agent are effected in the subject overlaps with the period during which the oncolytic effects of the virus are effected in the subject. Typically, each of these agents may exert oncolytic effects which endure over many (e.g. two to ten) days. Preferably, however, the two agents are administered within twenty-four hours of one another, and more preferably within several (e.g. two to ten) hours of each other. Of course, the agent and virus may be administered simultaneously, or nearly so, either in the form of a single composition comprising both the agent and the virus, or in the form of distinct compositions, one comprising the agent and the other comprising the virus.

The chemotherapeutic agents used in the methods, compositions, and kits of the invention include substantially all anti-neoplastic compositions and other compositions which have been demonstrated to exert chemical oncolytic activity (i.e. not transcriptionally-mediated oncolytic activity wherein transcription or reverse transcription of a nucleic acid is required). Because such chemotherapeutic agents are well known in the art, effective dosages and administration schedules are not described herein. Dosages, routes of administration, and administration schedules described in the prior art may be used, it being understood that the additivity or synergy demonstrated herein between such agents and oncolytic viruses allows use of chemotherapeutic agents at dosages lower than standard prior art dosages. For example, in addition to prior art dosages, dosages of chemotherapeutic agents from about 20% to 99% of prior art dosages may be used.

Similarly, oncolytic viruses other than adenoviruses are known in the art, and dosages, routes of administration, and administration schedules have been described. These known dosages, routes, and schedules may be used, again with the understanding that the synergy described herein between such viruses and chemotherapeutic agents allows use of lower dosages (e.g. 20% to 99%) of oncolytic viruses than are described in the prior art as being effective.

The subject may be any subject which has tumor cells and for which an oncolytic virus other than an adenovirus may be selected. The subject is preferably a human, although the subject may be substantially any other mammal, such as a primate or a laboratory animal such as a mouse, rat, rabbit, guinea pig, or the like. Methods of identifying oncolytic viruses are well known, and basically involve screening viruses to identify viruses which are capable of inducing death of a tumor cell in the subject (e.g. by inducing cytolysis or apoptosis in tumor cells).

The tumor cells which are to be killed in the subject may be substantially any tumor cells for which an oncolytic virus may be selected. Selection of an effective chemotherapeutic agent is typically less difficult, since many such agents exhibit oncolytic activity against a broad spectrun of tumor cell types. Still, the chemotherapeutic agent should be one which is known to exhibit oncolytic activity against the tumor cell type to be killed. Examples of tumor cells which may be killed in a subject using the methods, compositions, and kits of the invention include, but are not limited to, central nervous system tumor cells, mesothelioma cells, lung cancer cells, non-small cell lung cancer cells, undifferentiated lung carcinoma cells, large cell lung carcinoma cells, adenocarcinoma cells, bronchoalveolar cell lung carcinoma cells, liver cancer cells, localized non-central nervous system tumor cells, solid tumor cells, and ovarian cancer cells.

The chemotherapeutic agent used in the methods, compositions, and kits of the invention may, as discussed above, be substantially any agent which exhibits an oncolytic effect against the tumor cells in the subject and which does not inhibit or diminish the oncolytic effect of the oncolytic virus of the invention. Thus, the chemotherapeutic agent which can be used in the method described herein is not limited to one of those described herein. The agent may be any known or subsequently discovered chemotherapeutic agent. By way of example, known types chemotherapeutic agents include, for example, anthracyclines, alkylating agents, alkyl sulfonates, aziridines, ethylenimines, methylmelamines, nitrogen mustards, nitrosoureas, antibiotics, antimetabolites, folic acid analogs, purine analogs, pyrimidine analogs, enzymes, podophyllotoxins, platinum-containing agents, interferons, and interleukins.

Preferred types of chemotherapeutic agents include anthracyclines, folic acid analogs, platinum-containing agents, and alkylating agents. Preferred alkylating agents are bi-functional alkylating agents such as mitomycin C. Preferred folic acid analogs include, for example, dihydrofolate reductase inhibitors such as methotrexate.

Known chemotherapeutic agents include, but are not limited to, busulfan, improsulfan, piposulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethaamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluororacil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elfornithine, elliptinium acetate, etoglucid, etoposide, flutamide, gallium nitrate, hydroxyurea, interferon-alpha, interferon-beta, interferon-gamma, interleukin-2, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofiran, spirogermanium, paclitaxel, tamoxifen, teniposide, tenuazonic acid, triaziquone, 2,2',2"-trichlorotriethylamine, urethan, vinblastine, vincristine, and vindesine. Preferred agents include mechlorethamine, chlorambucil, cyclophosphamide, busulfan, improsulfan, piposulfan, melphalan, ifosfamide, methotrexate, 6-mercaptopurine, 5-fluorouracil, cytarabine, vinblastine, vincristine, etoposide, doxorubicin, daunomycin, bleomycin, mitomycin C, carmustine, lomustine, cisplatin, asparaginase, tamoxifen, flutamide, and paclitaxel. More preferred agents include doxorubicin, methotrexate, mitomycin C, cisplatin, 5-fluorouracil, paclitaxel, and cyclophosphamide.

It is understood that not every chemotherapeutic agent enhances the oncolytic activity of every oncolytic virus. Doxorubicin, for example, inhibits DNA dependent RNA polymerase. Inhibition of this enzyme may inhibit oncolytic viruses related to HSV-1, because HSV is known to use RNA polymerase II. As described herein, combined therapy with doxorubicin and HSV-1716 yielded oncolytic activity which was less than additive, but not antagonistic. Thus, when selecting an oncolytic virus and a chemotherapeutic agent, it is important to consider the biological activity of each, and to select an agent which does not inhibit, or only minimally inhibits, the oncolytic activity of the virus.

Substantially any known oncolytic virus may be used as the oncolytic virus of the invention, with the exception of adenoviruses, which are not included within the scope of the invention. Numerous oncolytic viruses are known in the art and are described, for example, in Kirn et al. (1999, In: *Gene Therapy of Cancer*, Academic Press, San Diego, Calif., pp. 235–248). By way of example, appropriate oncolytic viruses include type 1 herpes simplex viruses, type 2 herpes simplex viruses, vesicular stomatitis viruses, Newcastle disease viruses, vaccinia viruses, and mutant strains of these viruses. Preferably, the oncolytic virus is replication-selective or replication-competent, although replication-incompetent oncolytic viruses other than adenoviruses may also be used in the methods, compositions, and kits of the invention.

The oncolytic virus of the invention may, of course, comprise an exogenous nucleic acid (i.e. it may be an oncolytic virus vector). When the oncolytic virus comprises an exogenous nucleic acid, the nucleic acid preferably encodes an anti-oncogenic or oncolytic gene product. The gene product may be one (e.g. an antisense oligonucleotide) which inhibits growth or replication of only the cell infected by the virus, or it may be one (e.g. thymidine kinase) which exerts a significant bystander effect upon lysis of the cell infected by the virus.

Herpes simplex viruses are among the preferred viruses, particularly HSV-1 viruses which do not express functional ICP34.5. HSV-1 viruses which do not express this protein exhibit significantly less neurotoxicity than their wild type counterparts. When the oncolytic virus of the invention is a herpes simplex virus-1, it is preferably one which does not express functional ICP34.5 protein (e.g. HSV-1716) or one of the HSV-1 viruses described in Coukos et al., (1998, Gene Ther. Mol. Biol. 3:79–89). Exemplary HSV-1 viruses include HSV-1716, HSV-3410, HSV-3616, and HSV-4009. Other replication selective HSV-1 virus strains which may be used as the oncolytic virus of the invention include, by way of example and not limitation, HSV-R3616 (in which the gene encoding ICP34.5 is deleted), HSV-R47 (in which genes encoding proteins R3616 and ICP47 are deleted), HSV-G207 (in which genes encoding ICP34.5 and ribonucleotide reductase are deleted), HSV-7020, HSV-NVR10 (in which genes encoding 7020 and ICP47 are deleted), HSV-3616-UB (in which genes encoding ICP34.5 and uracil DNA glycosylase are deleted), HSV-G92A (in which the albumin promoter is a transcriptional regulated promoter), HSV-3616-IL-4, HSV-hrR3 (in which the gene encoding ribonucleotide reductase is deleted) and HSV strains which do not express functional ICP34.5 and which express a cytokine such as interleukin-2, interleukin-4, or GM-CSF.

The mutant virus which can be used in the methods described herein is not limited to one of the HSV-1 mutant strains described herein. Any replication-selective strain of a herpes simplex virus may be used. In addition to the HSV-1 mutant strains described herein, other HSV-1 mutant strains which are replication selective have been described in the art, although their use in combination with a chemotherapeutic agent has not. Furthermore, HSV-2 mutant strains such as, by way of example, HSV-2 strains HSV-2701, HSV-2616, and HSV-2604 may be used in the methods of the invention.

The oncolytic virus of the invention is, in one embodiment, replication-selective. It is understood that an oncolytic virus may be made replication-selective if replication of the virus is placed under the control of a regulator of gene expression such as, for example, a minimal enhancer/promoter region derived from the 5'-flank of the human PSA gene (e.g. see Rodriguez et al., 1997, Cancer Res. 57:2559–2563). By way of example, the main transcriptional unit of an HSV may be placed under transcriptional control of the tumor growth factor-β (TGF-β) promoter by operably linking HSV genes to the TGF-β promoter. It is known that certain tumor cells overexpress TGF-β, relative to non-tumor cells of the same type. Thus, an oncolytic virus wherein replication is subject to transcriptional control of the TGF-β promoter is replication-selective, in that it is more capable of replicating in the certain tumor cells than in non-tumor cells of the same type. Similar replication-selective oncolytic viruses may be made using any regulator of gene expression which is known to selectively cause overexpression in an affected cell. The replication-selective oncolytic virus may, for example, be an HSV-1 mutant in which a gene encoding ICP34.5 is mutated or deleted.

In a preferred embodiment of the methods, compositions, and kits of the invention, the oncolytic virus is HSV-1716 and the chemotherapeutic agent is mitomycin C.

Pharmaceutical Compositions and Kits

The invention includes a pharmaceutical composition useful for killing tumor cells in a subject having tumor cells. This composition comprises a chemotherapeutic agent and an oncolytic virus other than an adenovirus. The composition may be supplied as an already-mixed composition or as two separate compositions which are mixed shortly before or during administration to the subject. The invention also includes a kit comprising a chemotherapeutic agent and an oncolytic virus other than an adenovirus. The kit differs from the pharmaceutical composition in that the agent and virus in the kit need not be combined before or during administration to the subject, but may instead be administered to the subject at different times (e.g. within days, hours, or seconds). The kit may further include an instructional material which describes use of the agent and virus for killing tumor cells in a subject, appropriate dosages, appropriate routes of administration, appropriate dosing schedules, or the like.

Each of the chemotherapeutic agent and the oncolytic virus may be supplied, together or separately, in a variety of forms. Preferably, each is provided in the form of an injectable or infusible solution or suspension, or in a form which may be easily reconstituted (e.g. by addition of sterile water, saline, or buffer) to generate an injectable or infusible solution or suspension. When the tumor cells to be killed are located in a solid tumor, it is preferred that one or both of the chemotherapeutic agent and the oncolytic virus be supplied in the form of a solution or suspension which may be injected directly into the tumor tissue or in a form which be easily reconstituted to generate an injectable solution or suspension.

The invention encompasses the preparation and use of medicaments and pharmaceutical compositions comprising a chemotherapeutic agent and an oncolytic virus as active ingredients. Such a pharmaceutical composition may consist of the active ingredients alone, in a form suitable for administration to a subject, or the pharmaceutical composition may comprise the active ingredients and one or more pharmaceutically acceptable carriers, one or more additional ingredients, or some combination of these. Administration of one of these pharmaceutical compositions to a subject is useful for killing tumor cells in the subject, as described elsewhere in the present disclosure. The chemotherapeutic agent may be present in the pharmaceutical composition in the form of a physiologically acceptable ester or salt, such as in combination with a physiologically acceptable cation or anion, as is well known in the art.

As used herein, the term "pharmaceutically acceptable carrier" means a chemical composition with which one or more of the active ingredients may be combined and which, following the combination, can be used to administer the active ingredient(s) to a subject.

As used herein, the term "physiologically acceptable" ester or salt means an ester or salt form of a chemotherapeutic agent which is compatible with any other ingredients of the pharmaceutical composition and which is not deleterious to the subject to which the composition is to be administered.

The formulations of the pharmaceutical compositions described herein may be prepared by any method known or hereafter developed in the art of pharmacology. In general, such preparatory methods include the step of bringing the active ingredient(s) into association with a carrier or one or more other accessory ingredients, and then, if necessary or desirable, shaping or packaging the product into a desired single- or multi-dose unit.

Although the descriptions of pharmaceutical compositions provided herein are principally directed to pharmaceutical compositions which are suitable for ethical administration to humans, it will be understood by the skilled artisan that such compositions are generally suitable for administration to animals of all sorts. Modification of pharmaceutical compositions suitable for administration to humans in order to render the compositions suitable for administration to various animals is well understood, and the ordinarily skilled veterinary pharmacologist can design and perform such modification with merely ordinary, if any, experimentation. Subjects to which administration of the pharmaceutical compositions of the invention is contemplated include, but are not limited to, humans and other mammals such as primates, and laboratory animals such as mice, rats, guinea pigs, rabbits, and the like.

Pharmaceutical compositions that are useful in the methods of the invention may be prepared, packaged, or sold in formulations suitable for oral, rectal, vaginal, parenteral, topical, pulmonary, intranasal, buccal, ophthalmic, or another route of administration, depending on the anticipated site at or to which the composition is to be administered.

A pharmaceutical composition of the invention may be prepared, packaged, or sold in bulk, as a single unit dose, or as a plurality of single unit doses. As used herein, a "unit dose" is a discrete amount of the pharmaceutical composition comprising a predetermined amount of the active ingredient(s). The amount of the active ingredient(s) is generally equal to the dosage of the active ingredient(s) which would be administered to a subject or a convenient fraction of such a dosage such as, for example, one-half or one-third of such a dosage.

The relative amounts of the active ingredient(s), the pharmaceutically acceptable carrier, and any additional ingredients in a pharmaceutical composition of the invention will vary, depending upon the identity, size, and condition of the subject treated and further depending upon the route by which the composition is to be administered.

Controlled- or sustained-release formulations of a pharmaceutical composition of the invention may be made using conventional technology.

A formulation of a pharmaceutical composition of the invention suitable for oral administration may be prepared, packaged, or sold in the form of a discrete solid dose unit including, but not limited to, a tablet, a hard or soft capsule, a cachet, a troche, or a lozenge, each containing a predetermined amount of the active ingredient. Other formulations suitable for oral administration include, but are not limited to, a powdered or granular formulation, an aqueous or oily suspension, an aqueous or oily solution, or an emulsion.

As used herein, an "oily" liquid is one which comprises a carbon-containing liquid molecule and which exhibits a less polar character than water.

A tablet comprising the active ingredient may, for example, be made by compressing or molding the active ingredient, optionally with one or more additional ingredients. Compressed tablets may be prepared by compressing, in a suitable device, the active ingredient in a free-flowing form such as a powder or granular preparation, optionally mixed with one or more of a binder, a lubricant, an excipient, a surface active agent, and a dispersing agent. Molded tablets may be made by molding, in a suitable device, a mixture of the active ingredient, a pharmaceutically acceptable carrier, and at least sufficient liquid to moisten the mixture. Pharmaceutically acceptable excipients used in the manufacture of tablets include, but are not limited to, inert diluents, granulating and disintegrating agents, binding agents, and lubricating agents. Known dispersing agents include, but are not limited to, potato starch and sodium starch glycolate. Known surface active agents include, but are not limited to, sodium lauryl sulphate. Known diluents include, but are not limited to, calcium carbonate, sodium carbonate, lactose, microcrystalline cellulose, calcium phosphate, calcium hydrogen phosphate, and sodium phosphate. Known granulating and disintegrating agents include, but are not limited to, corn starch and alginic acid. Known binding agents include, but are not limited to, gelatin, acacia, pre-gelatinized maize starch, polyvinylpyrrolidone, and hydroxypropyl methylcellulose. Known lubricating agents include, but are not limited to, magnesium stearate, stearic acid, silica, and talc.

Tablets may be non-coated or they may be coated using known methods to achieve delayed disintegration in the gastrointestinal tract of a subject, thereby providing sustained release and absorption of the active ingredient. By way of example, a material such as glyceryl monostearate or glyceryl distearate may be used to coat tablets. Further by way of example, tablets may be coated using methods described in U.S. Pat. Nos. 4,256,108; 4,160,452; and 4,265,874 to form osmotically-controlled release tablets. Tablets may further comprise a sweetening agent, a flavoring agent, a coloring agent, a preservative, or some combination of these in order to provide pharmaceutically elegant and palatable preparation.

Hard capsules comprising the active ingredient may be made using a physiologically degradable composition, such as gelatin. Such hard capsules comprise the active ingredient, and may further comprise additional ingredients including, for example, an inert solid diluent such as calcium carbonate, calcium phosphate, or kaolin.

Soft gelatin capsules comprising the active ingredient may be made using a physiologically degradable composition, such as gelatin. Such soft capsules comprise the active ingredient, which may be mixed with water or an oil medium such as peanut oil, liquid paraffin, or olive oil.

Oral compositions may be made, using known technology, which specifically release orally-administered agents in the small or large intestines of a human patient. For example, formulations for delivery to the gastrointestinal system, including the colon, include enteric coated systems, based, e.g., on methacrylate copolymers such as poly (methacrylic acid, methyl methacrylate), which are only soluble at pH 6 and above, so that the polymer only begins to dissolve on entry into the small intestine. The site where such polymer formulations disintegrate is dependent on the rate of intestinal transit and the amount of polymer present. For example, a relatively thick polymer coating is used for delivery to the proximal colon (Hardy et al., 1987 Aliment. Pharmacol. Ther. 1:273–280). Polymers capable of providing site-specific colonic delivery can also be used, wherein the polymer relies on the bacterial flora of the large bowel to provide enzymatic degradation of the polymer coat and hence release of the drug. For example, azopolymers (U.S. Pat. No. 4,663,308), glycosides (Friend et al., 1984, J. Med. Chem. 27:261–268) and a variety of naturally available and modified polysaccharides (PCT GB 89/00581) may be used in such formulations.

Pulsed release technology such as that described in U.S. Pat. No. 4,777,049 may also be used to administer the active agent to a specific location within the gastrointestinal tract. Such systems permit drug delivery at a predetermined time and can be used to deliver the active agent, optionally together with other additives that my alter the local microenvironment to promote agent stability and uptake, directly to the colon, without relying on external conditions other than the presence of water to provide in vivo release.

Liquid formulations of a pharmaceutical composition of the invention which are suitable for oral administration may be prepared, packaged, and sold either in liquid form or in the form of a dry product intended for reconstitution with water or another suitable vehicle prior to use.

Liquid suspensions may be prepared using conventional methods to achieve suspension of the active ingredient in an aqueous or oily vehicle. Aqueous vehicles include, for example, water and isotonic saline. Oily vehicles include, for example, almond oil, oily esters, ethyl alcohol, vegetable oils such as arachis, olive, sesame, or coconut oil, fractionated vegetable oils, and mineral oils such as liquid paraffin. Liquid suspensions may further comprise one or more additional ingredients including, but not limited to, suspending agents, dispersing or wetting agents, emulsifying agents, demulcents, preservatives, buffers, salts, flavorings, coloring agents, and sweetening agents. Oily suspensions may further comprise a thickening agent. Known suspending agents include, but are not limited to, sorbitol syrup, hydrogenated edible fats, sodium alginate, polyvinylpyrrolidone, gum tragacanth, gum acacia, and cellulose derivatives such as sodium carboxymethylcellulose, methylcellulose, hydroxypropylmethylcellulose. Known dispersing or wetting agents include, but are not limited to, naturally-occurring phosphatides such as lecithin, condensation products of an alkylene oxide with a fatty acid, with a long chain aliphatic alcohol, with a partial ester derived from a fatty acid and a hexitol, or with a partial ester derived from a fatty acid and a hexitol anhydride (e.g. polyoxyethylene stearate, heptadecaethyleneoxycetanol, polyoxyethylene sorbitol monooleate, and polyoxyethylene sorbitan monooleate, respectively). Known emulsifying agents include, but are not limited to, lecithin and acacia. Known preservatives include, but are not limited to, methyl, ethyl, or n-propyl-para- hydroxybenzoates, ascorbic acid, and sorbic acid. Known sweetening agents include, for example, glycerol, propylene glycol, sorbitol, sucrose, and saccharin. Known thickening agents for oily suspensions include, for example, beeswax, hard paraffin, and cetyl alcohol.

Liquid solutions of the active ingredient in aqueous or oily solvents may be prepared in substantially the same manner as liquid suspensions, the primary difference being that the active ingredient is dissolved, rather than suspended in the solvent. Liquid solutions of the pharmaceutical composition of the invention may comprise each of the components described with regard to liquid suspensions, it being understood that suspending agents will not necessarily aid dissolution of the active ingredient in the solvent. Aqueous solvents include, for example, water and isotonic saline. Oily solvents include, for example, almond oil, oily esters, ethyl alcohol, vegetable oils such as arachis, olive, sesame, or coconut oil, fractionated vegetable oils, and mineral oils such as liquid paraffin.

Powdered and granular formulations of a pharmaceutical preparation of the invention may be prepared using known methods. Such formulations may be administered directly to a subject, used, for example, to form tablets, to fill capsules, or to prepare an aqueous or oily suspension or solution by addition of an aqueous or oily vehicle thereto. Each of these formulations may further comprise one or more of dispersing or wetting agent, a suspending agent, and a preservative. Additional excipients, such as fillers and sweetening, flavoring, or coloring agents, may also be included in these formulations.

A pharmaceutical composition of the invention may also be prepared, packaged, or sold in the form of oil-in-water emulsion or a water-in-oil emulsion. The oily phase may be a vegetable oil such as olive or arachis oil, a mineral oil such as liquid paraffin, or a combination of these. Such compositions may further comprise one or more emulsifying agents such as naturally occurring gums such as gum acacia or gum tragacanth, naturally-occurring phosphatides such as soybean or lecithin phosphatide, esters or partial esters derived from combinations of fatty acids and hexitol anhydrides such as sorbitan monooleate, and condensation products of such partial esters with ethylene oxide such as polyoxyethylene sorbitan monooleate. These emulsions may also contain additional ingredients including, for example, sweetening or flavoring agents.

A pharmaceutical composition of the invention may be prepared, packaged, or sold in a formulation suitable for rectal administration. Such a composition may be in the form of, for example, a suppository, a retention enema preparation, and a solution for rectal or colonic irrigation.

Suppository formulations may be made by combining the active ingredient with a non-irritating pharmaceutically acceptable excipient which is solid at ordinary room temperature (i.e. about 20° C.) and which is liquid at the rectal temperature of the subject (i.e. about 37° C. in a healthy human). Suitable pharmaceutically acceptable excipients include, but are not limited to, cocoa butter, polyethylene glycols, and various glycerides. Suppository formulations may further comprise various additional ingredients including, but not limited to, antioxidants and preservatives.

Retention enema preparations or solutions for rectal or colonic irrigation may be made by combining the active ingredient with a pharmaceutically acceptable liquid carrier. As is well known in the art, enema preparations may be administered using, and may be packaged within, a delivery device adapted to the rectal anatomy of the subject. Enema preparations may further comprise various additional ingredients including, but not limited to, antioxidants and preservatives.

A pharmaceutical composition of the invention may be prepared, packaged, or sold in a formulation suitable for vaginal administration. Such a composition may be in the form of, for example, a suppository, an impregnated or coated vaginally-insertable material such as a tampon, a douche preparation, or a solution for vaginal irrigation.

Methods for impregnating or coating a material with a chemical composition are known in the art, and include, but are not limited to methods of depositing or binding a chemical composition onto a surface, methods of incorporating a chemical composition into the structure of a material during the synthesis of the material (i.e. such as with a physiologically degradable material), and methods of absorbing an aqueous or oily solution or suspension into an absorbent material, with or without subsequent drying.

Douche preparations or solutions for vaginal irrigation may be made by combining the active ingredient with a pharmaceutically acceptable liquid carrier. As is well known in the art, douche preparations may be administered using, and may be packaged within, a delivery device adapted to the vaginal anatomy of the subject. Douche preparations may further comprise various additional ingredients including, but not limited to, antioxidants, antibiotics, antifungal agents, and preservatives.

As used herein, "parenteral administration" of a pharmaceutical composition includes any route of administration characterized by physical breaching of a tissue of a subject and administration of the pharmaceutical composition through the breach in the tissue. Parenteral administration thus includes, but is not limited to, administration of a pharmaceutical composition by injection of the composition, by application of the composition through a surgical incision, by application of the composition through a tissue-penetrating non-surgical wound, and the like. In particular, parenteral administration is contemplated to include, but is not limited to, subcutaneous, intraperitoneal, intravenous, intraarterial, intramuscular, or intrasternal injection and intravenous, intraarterial, or kidney dialytic infusion techniques.

Formulations of a pharmaceutical composition suitable for parenteral administration comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampules, in multi-dose containers containing a preservative, or in single-use devices for auto-injection or injection by a medical practitioner. Formulations for parenteral administration include, but are not limited to, suspensions, solutions, emulsions in oily or aqueous vehicles, pastes, and implantable sustained-release or biodegradable formulations. Such formulations may further comprise one or more additional ingredients including, but not limited to, suspending, stabilizing, or dispersing agents. In one embodiment of a formulation for parenteral administration, the active ingredient is provided in dry (i.e. powder or granular) form for reconstitution with a suitable vehicle (e.g. sterile pyrogen-free water) prior to parenteral administration of the reconstituted composition.

The pharmaceutical compositions may be prepared, packaged, or sold in the form of a sterile injectable aqueous or oily suspension or solution. This suspension or solution may be formulated according to the known art, and may comprise, in addition to the active ingredient, additional ingredients such as the dispersing agents, wetting agents, or suspending agents described herein. Such sterile injectable formulations may be prepared using a non-toxic parenterally-acceptable diluent or solvent, such as water or 1,3-butane diol, for example. Other acceptable diluents and solvents include, but are not limited to, Ringer's solution, isotonic sodium chloride solution, and fixed oils such as synthetic mono- or di-glycerides. Other parentally-administrable formulations which are useful include those which comprise the active ingredient in microcrystalline form, in a liposomal preparation, or as a component of a biodegradable polymer systems. Compositions for sustained release or implantation may comprise pharmaceutically acceptable polymeric or hydrophobic materials such as an emulsion, an ion exchange resin, a sparingly soluble polymer, or a sparingly soluble salt.

Formulations suitable for topical administration include, but are not limited to, liquid or semi-liquid preparations such as liniments, lotions, oil-in-water or water-in-oil emulsions such as creams, ointments or pastes, and solutions or suspensions. Topically-administrable formulations may, for example, comprise from about 1% to about 10% (w/w) active ingredient, although the concentration of the active ingredient may be as high as the solubility limit of the active ingredient in the solvent. Formulations for topical administration may further comprise one or more of the additional ingredients described herein.

A pharmaceutical composition of the invention may be prepared, packaged, or sold in a formulation suitable for pulmonary administration via the buccal cavity. Such a formulation may comprise dry particles which comprise the active ingredient and which have a diameter in the range from about 0.5 to about 7 nanometers, and preferably from about 1 to about 6 nanometers. Such compositions are conveniently in the form of dry powders for administration using a device comprising a dry powder reservoir to which a stream of propellant may be directed to disperse the powder or using a self-propelling solvent/powder-dispensing container such as a device comprising the active ingredient dissolved or suspended in a low-boiling propellant in a sealed container. Preferably, such powders comprise particles wherein at least 98% of the particles by weight have a diameter greater than 0.5 nanometers and at least 95% of the particles by number have a diameter less than 7 nanometers. More preferably, at least 95% of the particles by weight have a diameter greater than 1 nanometer and at least 90% of the particles by number have a diameter less than 6 nanometers. Dry powder compositions preferably include a solid fme powder diluent such as sugar and are conveniently provided in a unit dose form.

Low boiling propellants generally include liquid propellants having a boiling point of below 65° F. at atmospheric pressure. Generally the propellant may constitute 50 to 99.9% (w/w) of the composition, and the active ingredient may constitute 0.1 to 20% (w/w) of the composition. The propellant may further comprise additional ingredients such as a liquid non-ionic or solid anionic surfactant or a solid diluent (preferably having a particle size of the same order as particles comprising the active ingredient).

Pharmaceutical compositions of the invention formulated for pulmonary delivery may also provide the active ingredient in the form of droplets of a solution or suspension. Such formulations may be prepared, packaged, or sold as aqueous or dilute alcoholic solutions or suspensions, optionally sterile, comprising the active ingredient, and may conveniently be administered using any nebulization or atomization device. Such formulations may further comprise one or more additional ingredients including, but not limited to, a flavoring agent such as saccharin sodium, a volatile oil, a buffering agent, a surface active agent, or a preservative such as methylhydroxybenzoate. The droplets provided by this route of administration preferably have an average diameter in the range from about 0.1 to about 200 nanometers.

As used herein, "additional ingredients" include, but are not limited to, one or more of the following: excipients; surface active agents; dispersing agents; inert diluents; granulating and disintegrating agents; binding agents; lubricating agents; sweetening agents; flavoring agents; coloring agents; preservatives; physiologically degradable compositions such as gelatin; aqueous vehicles and solvents; oily vehicles and solvents; suspending agents; dispersing or wetting agents; emulsifying agents, demulcents; buffers; salts; thickening agents; fillers; emulsifying agents; antioxidants; antibiotics; antifungal agents; stabilizing agents; and pharmaceutically acceptable polymeric or hydrophobic materials. Other "additional ingredients" which may be included in the pharmaceutical compositions of the invention are known in the art and described, for example in Genaro, ed., 1985, *Remington's Pharmaceutical Sciences,* Mack Publishing Co., Easton, Pa., which is incorporated herein by reference.

It is understood that the ordinarily skilled physician or veterinarian will readily determine and prescribe effective amounts of the chemotherapeutic agent and oncolytic virus of the invention to kill tumor cells in the subject. In so proceeding, the physician or veterinarian may, for example, prescribe relatively low doses at first, subsequently increasing the doses until an appropriate response is obtained. It is further understood, however, that the specific dose levels for any particular subject will depend upon a variety of factors including the activities of the specific agent and virus employed, the age, body weight, general health, gender, and diet of the subject, the time of administration, the route of administration, the rate of excretion, any drug combination, and the extent, density, location, and type of tumor cells to be killed.

Another aspect of the invention relates to a kit comprising a pharmaceutical composition of the invention and an instructional material. As used herein, an "instructional material" includes a publication, a recording, a diagram, or any other medium of expression which is used to communicate the usefulness of the pharmaceutical composition of the invention for killing tumor cells in a subject. The instructional material may also, for example, describe an appropriate dose of the pharmaceutical composition of the invention. The instructional material of the kit of the invention may, for example, be affixed to a container which contains a pharmaceutical composition of the invention or be shipped together with a container which contains the pharmaceutical composition. Alternatively, the instructional material may be shipped separately from the container with the intention that the instructional material and the pharmaceutical composition be used cooperatively by the recipient.

The invention also includes a kit comprising a pharmaceutical composition of the invention and a delivery device for delivering the composition to a subject. By way of example, the delivery device may be a squeezable spray bottle, a metered-dose spray bottle, an aerosol spray device, an atomizer, a dry powder delivery device, a self-propelling solvent/powder-dispensing device, a syringe, a needle, a tampon, or a dosage measuring container. The kit may further comprise an instructional material as described herein.

The invention is now described with reference to the following Example. This Example is provided for the purpose of illustration only, and the invention should in no way be construed as being limited to this Example, but rather should be construed to encompass any and all variations which become evident as a result of the teaching provided herein.

EXAMPLE

HSV-based oncolytic therapy is a novel approach to treatment malignancies such as glioma, melanoma, and mesothelioma (Martuza et al., 1991, Science 252:854–856; Randazzo et al., 1995, Virology 211:94–101; Kucharczuk et al., 1997, Cancer Res. 57:466–471). In the experiments presented in this Example, a replication-restricted herpes simplex virus type 1 mutant (HSV-1716) demonstrated efficacy both in vitro and in vivo against human non-small cell lung cancer (NSCLC) cells. HSV-1716 is an HSV-1 mutant strain which does not express the protein designated ICP34.5 and which therefore exhibits markedly attenuated neurovirulence. This mutant strain also replicates 30–100 times more efficiently in dividing cells than stationary cells, relative to wild type HSV-1.

Oncolytic treatment using one of four chemotherapeutic agents was combined with HSV-1716-mediated oncolytic treatment. The four agents assessed in these experiments were mitomycin C, cisplatinum (a.k.a. cisplatin), methotrexate, and doxorubicin. Each of these four agents is known to induce apoptosis in susceptible cells by distinct mechanisms. It is also known HSV-1 induces apoptosis in some cell lines, and lysis in other cell lines (Galvan et al., 1998, Proc. Natl. Acad. Sci. USA 95:3931–3936).

These experiments demonstrate that treating NSCLC cells with both HSV-1716 and a chemotherapeutic agent enhanced the oncolytic effect of the individual treatments. The enhancement was at least additive for each combination, and was synergistic with regard to the combination of mitomycin C and HSV-1716 treatments.

The materials and methods used in the experiments presented in this Example are now described.
Reagents Mitomycin C, methotrexate, and doxorubicin were obtained from Calbiochem (La Jolla, Calif.). Cisplatinum was obtained from Sigma Chemical Co. (St. Louis, Mo.). Each drug was dissolved or suspended in phosphate buffered saline.
Cells and Virus Human non-small cell lung cancer (NSCLC) cell lines, such as A549 (undifferentiated lung carcinoma), Calu-1 (squamous cell carcinoma), H460 (large cell carcinoma), Calu-3 (adenocarcinoma) and H322 (bronchoalveolar carcinoma), representing each of the major histopathological types, were obtained from American Type Culture Collection (Rockville, Md.) and maintained as recommended. HSV-1716, a mutant HSV-1 lacking both copies of the gene coding ICP34.5, was generated as described (Kucharczuk et al., 1997, Cancer Res. 57:466–471).
In vitro Cell Viability Assay The combined effect of each of the four chemotherapeutic agents with HSV-1716 in the human large cell lung carcinoma line designated H460 was assessed as follows. Cells were incubated in 96-well plates at a density of about 3,000 cells per well. Twenty-four hours later, the cells were infected at selected values of multiplicity of infection (MOI) for one hour in serum-free medium. Individual chemotherapeutic agents were then added to selected wells. When the cells in the control well were confluent (i.e. generally between days 3 and 6), the percentage of viable cells was assessed in all wells.

Cell viability was assessed by colorimetric assay, using a CellTiter 96™ Aqueous kit obtained from Promega (Madison, Wis.) per the manufacturer's instructions. The percentage of growth was defined as 100 times the ratio of the mean absorbance of eighteen agent-treated wells to the mean absorbance of six non-agent-treated control wells.

In order to observe the effects of combined chemotherapeutic agent treatment and HSV-1716 treatment, doses of each agent which (in the absence of HSV-1716) allowed at least 50% cell growth were combined with doses of HSV-1716 which (in the absence of a chemotherapeutic agent) allowed at least 50% cell growth. Combined treatment of cells with mitomycin C and HSV-1716 was performed using four other human NSCLC cell lines, namely those designated Calu-1, Calu-3, H322, and A549. Each treatment experiment was performed at least twice.

To determine whether chemotherapeutic agents augment the cytolytic efficacy of different HSV mutants, we compared the efficacy of mitomycin C combined with HSV mutants including HSV-1716, HSV-3616, HSV-4009, HSV-3410 and HSV-G207 in A549 cells. The combination of mitomycin C and any of these viruses was approximately additive, with the combination of HSV-1716 or HSV-G207 and mitomycin C being the most effective. This combined effect often varied depending on the dose of drug and the MOI, and can be even synergistic in some circumstances.

In vivo Xenograft Flank Model

The combined effects of mitomycin C and HSV-1716 using NSCLC tumors was assessed in vivo as follows. Cells of line H460 were implanted subcutaneously in the flanks of severe combined immunodeficient (SCID) mice. The tumors which developed had a mean volume of 160 to 170 cubic millimeters. HSV-1716 was injected directly into individual tumors at a dose of $4 \times 10^6$ plaque forming units (pfu) in 200 microliters of medium. Control mice were injected with medium alone. Twenty-four hours later, 0.17 milligrams per kilogram body weight mitomycin C or an equivalent amount of PBS was administered to separate groups of HSV-treated and control mice. Tumor volume was estimated in all mice at regular intervals. Tumor volume in cubic millimeters was estimated using the formula $$0.4 \times TL_{mm} \times TW_{mm}$$

where $TL_{mm}$ was tumor length in millimeters and $TW_{mm}$ was tumor width in millimeters. Tumor growth curves were generated using the estimated values for tumor volume. After a period of 3–4 weeks, mice were sacrificed and their tumors were weighed.

One Step Growth Curve

H460 cells were incubated overnight in six-well plates at a density of about 300,000 cells per well under standard culture condition. Following this incubation, the cells were infected with HSV-1716 at an MOI of 0.1 pfu. In a parallel experiment with five different experimental arms, the following procedures were performed. In the first and second arms, the cells were incubated in the presence of 0.1 micromolar mitomycin C or an equivalent additional volume of culture medium. Mediun or medium containing mitomycin C was added to the wells for 3 hours, either immediately before (in the first arm) or immediately following (in the second arm) infection of the cells with HSV-1716. In the other three arms, medium containing 0.1, 1.0, or 3.0 micromolar mitomycin C was added to the wells for 48 hours following infection of the cells with HSV-1716.

Cells were harvested from individual wells 1, 6, 19, 24, or 48 hours following infection. Cells were harvested by scraping cells from the walls of their well into the medium contained within the well. Harvested cells were stored at −80° C. Cell samples were titered by black plaque assay using baby hamster kidney cell (BHK) monolayers as described (Kucharczuk et al., 1997, Cancer Res. 57:466–471).

The results of the experiments presented in this Example are now described.

Mitomycin C exhibits a synergistic effect in combination with HSV-1716 in H460 and A549 Cells in vitro In the experiments presented in this Example, the cytolytic effects of several concentrations of chemotherapeutic agents were assessed in combination with several MOI values for HSV-1716 in order to determine whether the effects of the agents and the virus were synergistic, additive, or antagonistic. For most of the combinations tested, the effects of the agent and virus was at least additive.

The effects of mitomycin C and HSV-1716 were synergistic, both in cell line H460 and A549. For example, HSV-1716 at an MOI of 0.1 exhibited 85.9% cell survival, and mitomycin C at 0.1 micromolar exhibited 96.7% cell survival for cell line H460. However, when cells H460 cells were treated with both 0.1 micromolar mitomycin C and HSV-1716 at an MOI of 0.1, only 53.6% of cells survived. Combined treatment of H460 cells with cisplatinum and HSV-1716 exhibited weak synergism under certain conditions, and an additive effect under other conditions.

Combined treatment with mitomycin C and HSV-1716 was assessed in four other NSCLC cell lines (Calu-1, Calu-3, H322, and A549) which represented the major histopathological types of non-small cell lung cancer. Synergistic effects were demonstrated in cell line A549, but not in the other three cell lines, wherein an additive effect was observed. No antagonistic effect of combining mitomycin C and HSV-1716 was observed under any conditions.

Mitomycin C Augment HSV-based Oncolytic Effect in an in vivo Xenograft Model

In order to assess the oncolytic effect of mitomycin C in combination with HSV-1716, a murine xenograft model was used. In preliminary experiments, doses of mitomycin C and HSV-1716 that were sufficient to yield 70% to 80% cell survival were determined. These doses were designated 'sufficient doses.' H460 tumor cells were injected into the flanks of SCID mice. Seven days later, the mean tumor volume was estimated to be about 160 to 170 cubic centimeters. At that time, about $4 \times 10^6$ pfu of HSV-1716 or an equivalent volume of culture medium was injected into individual tumors. Twenty-four hours later, a solution comprising PBS was intravenously administered to selected mice, and a solution comprising about 0.17 milligrams per kilogram body weight of mitomycin C in PBS was intravenously administered to the remaining mice.

Figure 1:
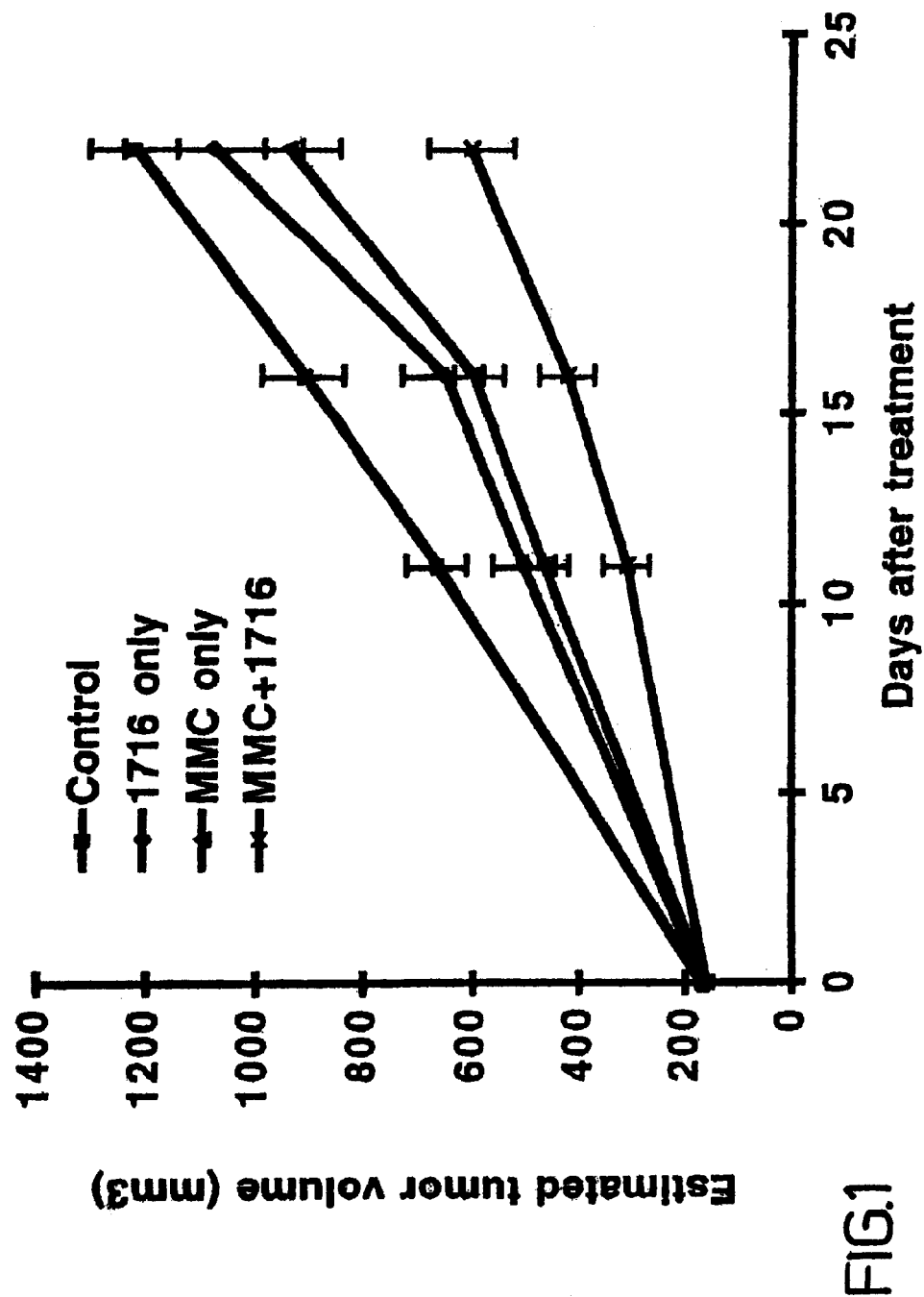
FIG. 1 is a graph which depicts the estimated tumor burden in SCID mice into the flanks of which H460 cells had been injected at day 0. The four lines correspond to four groups of mice which were treated differently. Cell culture medium was injected into the tumors of the first group of mice ("control") on day 7, and phosphate buffered saline (PBS) was intravenously administered to these mice on day 8. Cell culture medium comprising HSV-1716 was injected into the tumors of the second group of mice ("1716 only")

Tumor volume was estimated at regular intervals, and is indicated in FIG. 1. Mice were sacrificed and their tumors were weighed 22 days following injection of tumor cells. Final mean tumor burden in control mice was 1.406±0.079 grams (n=14). Treatment with HSV-1716 alone reduced tumor burden 19.8% to 1.127±0.139 grams (n=14; p=0.03 versus control). Treatment with mitomycin C alone reduced tumor burden 20.2% to 1.122±0.070 grams (n=14; p=0.03 versus control). When tumors were treated with both mitomycin C and HSV-1716, the tumor burden was reduced to 0.793±0.047 gram (n=14; p=0.01 versus HSV-1716 alone and p=0.01 versus mitomycin C alone). Thus, the tumor burden in animals which were treated with both mitomycin C and HSV-1716 was significantly lower than the tumor burden in animals treated with agent alone. Combined treatment reduced tumor burden 43.6%, relative to the control. Individual treatment with HSV-1716 reduced tumor burden only 20.2%, and individual treatment with mitomycin C alone reduced tumor burden only 21.8%.

Low Dose Mitomycin C (0.1 micromolar) Neither Augmented nor Reduced Burst Size of HSV-1716 in Cell Lines H460 and A549

In order to examine what effect mitomycin C might have on viral replication, one step growth curve experiments were performed. H460 cells were infected with HSV-1716 at an MOI of 0.1, and then 0.1 or 1.0 or 3.0 micromolar mitomycin C was added to the cell culture medium. At selected times, cells were harvested and titered by black plaque assay as described herein. The results of these assays are shown in FIG. 2. Burst size following pre-treatment of cells with 0.1 micromolar mitomycin C for 3 hours or following post-treatment with 0.1 micromolar mitomycin C for either 3 hours or 48 hours did not differ significantly from the burst size in control cells (42.1, 57.1, 53.3 and 60.3, respectively). Addition of 1.0 or 3.0 micromolar mitomycin C for 48 hours after infection reduced burst size (13.7 and 0.2, respectively). These results were consistent with data generated in analogous experiments involving cell line A549. Although high dose mitomycin C may lessen burst size, low dose mitomycin C (e.g. 0.1 micromolar) did not augment or inhibit HIV-1716 replication.

Without wishing to be bound by any particular theory of operation, it is believed that the synergistic effect of combining mitomycin C and HSV-1716 treatment of tumor cells may be explained as follows. HSV infection may increase D-T-diaphorase activity. This enzyme is known to augment activity of mitomycin C. Mitomycin C is also known to be activated to cytotoxic intermediates in a hypoxic environment. Upon infection by HSV-1716, the cellular environment becomes hypoxic and acidic, and thereby augments the cytotoxicity of mitomycin C.

The experiments presented in this Example demonstrate the usefulness of administering both a chemotherapeutic agent such as mitomycin C and an oncolytic virus such as HSV-1716 to a subject having tumor cells in order to kill at least some of the tumor cells.

The disclosures of each and every patent, patent application, and publication cited herein are hereby incorporated herein by reference in their entirety.

While this invention has been disclosed with reference to specific embodiments, it is apparent that other embodiments and variations of this invention may be devised by others skilled in the art without departing from the true spirit and scope of the invention. The appended claims are intended to be construed to include all such embodiments and equivalent variations.

What is claimed is:

1. A method of killing tumor cells in a subject having tumor cells, said method comprising administering to the subject
   a) a chemotherapeutic agent and
   b) a herpes virus
whereby tumor cells are killed.

2. The method of claim 1, wherein said chemotherapeutic agent is selected from the group consisting of an anthracycline, an alkylating agent, an alkyl sulfonate, an aziridine, an ethylenimine, a methylmelamine, a nitrogen mustard, a nitrosourea, an antibiotic, an antimetabolite, a folic acid analog, a purine analog, a pyrimidine analog, an enzyme, a podophyllotoxin, a platinum-containing agent, an interferon, and an interleukin.

3. The method of claim 2, wherein said chemotherapeutic agent is selected from the group consisting of an anthracycline, a folic acid analog, an alkylating agent, and a platinum-containing agent.

4. The method of claim 3, wherein said alkylating agent is a bi-functional alkylating agent.

5. The method of claim 4, wherein said bi-functional alkylating agent is mitomycin C.

6. The method of claim 3, wherein said folic acid analog is a dihydrofolate reductase inhibitor.

7. The method of claim 1, wherein said chemotherapeutic agent is selected from the group consisting of busulfan, improsulfan, piposulfan, benzodepa, carboquone, meturedepa, uredepa, altretamine, triethylenemelamine, triethylenephosphoramide, triethylenethiophosphoramide, trimethylolomelamine, chlorambucil, chlornaphazine, cyclophosphamide, estramustine, ifosfamide, mechlorethamine, mechlorethamine oxide hydrochloride, melphalan, novembichin, phenesterine, prednimustine, trofosfamide, uracil mustard, carmustine, chlorozotocin, fotemustine, lomustine, nimustine, ranimustine, dacarbazine, mannomustine, mitobronitol, mitolactol, pipobroman, aclacinomycins, actinomycin F(1), anthramycin, azaserine, bleomycin, cactinomycin, carubicin, carzinophilin, chromomycin, dactinomycin, daunorubicin, daunomycin, 6-diazo-5-oxo-1-norleucine, doxorubicin, epirubicin, mitomycin C, mycophenolic acid, nogalamycin, olivomycin, peplomycin, plicamycin, porfiromycin, puromycin, streptonigrin, streptozocin, tubercidin, ubenimex, zinostatin, zorubicin, denopterin, methotrexate, pteropterin, trimetrexate, fludarabine, 6-mercaptopurine, thiamiprine, thioguanine, ancitabine, azacitidine, 6-azauridine, carmofur, cytarabine, dideoxyuridine, doxifluridine, enocitabine, floxuridine, fluororacil, tegafur, L-asparaginase, pulmozyme, aceglatone, aldophosphamide glycoside, aminolevulinic acid, amsacrine, bestrabucil, bisantrene, carboplatin, cisplatin, defofamide, demecolcine, diaziquone, elfornithine, elliptinium acetate, etoglucid, etoposide, flutamide, gallium nitrate, hydroxyurea, interferon-alpha, interferon-beta, interferon-gamma, interleukin-2, lentinan, lonidamine, mitoguazone, mitoxantrone, mopidamol, nitracrine, pentostatin, phenamet, pirarubicin, podophyllinic acid, 2-ethylhydrazide, procarbazine, razoxane, sizofiran, spirogermanium, paclitaxel, tamoxifen, teniposide, tenuazonic acid, triaziquone, 2,2',2"-trichlorotriethylamine, urethan, vinblastine, vincristine, and vindesine.

8. The method of claim 7, wherein said chemotherapeutic agent is selected from the group consisting of mechlorethamine, chlorambucil, cyclophosphamide, busulfan, improsulfan, piposulfan, melphalan, ifosfamide, methotrexate, 6-mercaptopurine, 5-fluorouracil, cytarabine, vinblastine, vincristine, etoposide, doxorubicin, daunomycin, bleomycin, mitomycin C, carmustine, lomustine, cisplatin, asparaginase, tamoxifen, flutamide, and paclitaxel.

9. The method of claim 8, wherein said chemotherapeutic agent is selected from the group consisting of doxorubicin, methotrexate, mitomycin C, cisplatin, 5-fluorouracil, paclitaxel, and cyclophosphamide.

10. The method of claim 1, wherein said oncolytic virus is selected from the group consisting of a herpes simplex virus-1, a herpes simplex virus-2, a vesicular stomatitis virus, and a vaccinia virus.

11. The method of claim 10, wherein said herpes simplex virus-1 does not express functional ICP34.5.

12. The method of claim 10, wherein said herpes simplex virus-1 is selected from the group consisting of HSV-1716, HSV-3410, HSV-3616, HSV-R3616, HSV-R47, HSV-G207, HSV-7020, HSV-NVR10,, HSV-G92A, HSV-3616-IL-4, and HSV-hrR3.

13. The method of claim 12, wherein said herpes simplex virus-1 is HSV-1716.

14. The method of claim 10, wherein said herpes simplex virus-2 is selected from the group consisting of strain 2701, strain 2616, and strain 2604.

15. The method of claim 1, wherein said oncolytic virus is HSV-1716 and wherein said chemotherapeutic agent is mitomycin C.

16. The method of claim 1, wherein the subject is a mammal.

17. The method of claim 16, wherein the mammal is a human.

18. The method of claim 1, wherein the tumor cells are selected from the group consisting of central nervous system tumor cells, mesothelioma cells, lung cancer cells, non-small cell lung cancer cells, undifferentiated lung carcinoma cells, large cell lung carcinoma cells, adenocarcinoma cells, bronchoalveolar cell lung carcinoma cells, liver cancer cells, localized non-central nervous system tumor cells, solid tumor cells, and ovarian cancer cells.

19. The method of claim 18, wherein the tumor cells are non-small cell lung cancer cells.

* * * * *

UNITED STATES PATENT AND TRADEMARK OFFICE
CERTIFICATE OF CORRECTION

| | | |
|---|---|---|
| PATENT NO. | : 6,428,968 B1 | |
| APPLICATION NO. | : 09/435797 | |
| DATED | : August 6, 2002 | |
| INVENTOR(S) | : Katherine Molnar-Kimber, Larry Kaiser and Takane Toyolzumi | |

It is certified that error appears in the above-identified patent and that said Letters Patent is hereby corrected as shown below:

In column 22, lines 55-62, please amend claim 10 to state:

-- 10. The method of claim 1, wherein said herpes virus is selected from the group consisting of a herpes simplex virus-1, and a herpes simplex virus-2. --

In column 23, lines 8-10, please amend claim 15 to state:

-- 15. The method of claim 1, wherein said herpes virus is HSV-1716 and wherein said chemotherapeutic agent is mitomycin C. --

Signed and Sealed this
Seventeenth Day of May, 2011

David J. Kappos
*Director of the United States Patent and Trademark Office*